United States Patent [19]

Sachs et al.

[11] Patent Number: 6,068,856
[45] Date of Patent: May 30, 2000

[54] ORAL PHARMACEUTICAL COMPOSITION WITH DELAYED RELEASE OF ACTIVE INGREDIENT FOR PANTOPRAZOLE

[75] Inventors: George Sachs, Encino, Calif.; Rango Dietrich, Constance, Germany

[73] Assignee: BYK Gulden Chemische Fabrik GmbH, Constance, Germany

[21] Appl. No.: 09/042,090

[22] Filed: Mar. 13, 1998

Related U.S. Application Data

[62] Division of application No. 08/498,386, Jul. 5, 1995, Pat. No. 5,945,124.

[51] Int. Cl.⁷ .............................. A61K 9/28; A61K 9/32; A61K 9/36
[52] U.S. Cl. ................... 424/474; 424/475; 424/480; 424/482; 424/490; 424/494; 424/495; 424/497
[58] Field of Search .................. 424/464, 465, 424/474, 468, 480, 482, 472, 497, 494, 495

[56] References Cited

U.S. PATENT DOCUMENTS

| | | | |
|---|---|---|---|
| 5,385,739 | 1/1995 | Debregeas et al. | 424/494 |
| 5,447,923 | 9/1995 | Catrenich et al. | 514/147 |
| 5,582,837 | 12/1996 | Shell | 424/451 |

FOREIGN PATENT DOCUMENTS

| | | | |
|---|---|---|---|
| 0 342 522 A1 | 5/1988 | European Pat. Off. | A61K 31/44 |
| 0519365 | 12/1992 | European Pat. Off. | A61K 9/20 |
| 92/03135 | 3/1992 | WIPO | A61K 31/44 |
| 94/24867 | 11/1994 | WIPO | A01N 43/40 |
| 97/48380 | 12/1997 | WIPO | A61K 9/00 |

OTHER PUBLICATIONS

International Search Report dated Nov. 15, 1996.

*Primary Examiner*—Thurman K. Page
*Assistant Examiner*—James M. Spear
*Attorney, Agent, or Firm*—Jacobson, Price, Holman & Stern, PLLC

[57] ABSTRACT

An oral pharmaceutical composition of pantoprazole in pellet or tablet form, wherein the pantoprazole is at least partly in slow-release form, is distinguished, on combined administration with an antimicrobially-active ingredient, by an enhanced action of rapid onset against disorders caused by Helicobacter.

16 Claims, No Drawings

ORAL PHARMACEUTICAL COMPOSITION WITH DELAYED RELEASE OF ACTIVE INGREDIENT FOR PANTOPRAZOLE

RELATED APPLICATION

This application is a division of application Ser. No. 08/498,386, filed Jul. 5, 1995, now U.S. Pat. No. 5,945,124, and is related to Applicants' concurrently-filed application Ser. No. 08/498,391.

FIELD OF THE INVENTION

The present invention relates to oral pharmaceutical compositions in pellet or tablet form for combined use of pantoprazole with an antimicrobially-active ingredient for the treatment of disorders caused by Helicobacter.

BACKGROUND

Pyridin-2-ylmethylsulfinyl-1H-benzimidazoles, as disclosed, for example, in EP-A 0005129, EP-A 0166287 and EP-A 0268956 are becoming increasingly important, because of their $H^+/K^+$ ATPase-inhibiting action, for the therapy of diseases which originate from increased gastric acid secretion. Examples of active ingredients which are already commercially available from this group are omeprazole (INN), lansoprazole (INN) and pantoprazole (INN). These active ingredients are also called irreversible proton pump inhibitors.

Control of the microbe, *Helicobacter pylori*, which is thought to be responsible for certain gastric disorders, by combined use of an antimicrobially-active ingredient which is active against *Helicobacter pylori* and of an agent which reduces gastric acid has been regarded as the method of choice for some time.

EP-A 0519365 proposes (for the active ingredient pantoprazole) a formulation based on the principle of an alkaline core coated with a water-soluble intermediate layer and with an interic layer, where improved stability is achieved by using polyvinylpyrrolidone and/or hydroxypropylmethylcellulose as binder for the alkaline core.

EP-A 0342522 discloses a formulation for acid-sensitive benzimidazoles, in which an intermediate layer is located between the alkaline core and the enteric coating and is composed of a film-forming material which has only low solubility in water, such as ethylcellulose and polyvinyl acetate, and of a fine-particle inorganic or organic material which is suspended therein and has low solubility in water, such as magnesium oxide, silicon oxide or sucrose fatty acid esters.

JP-A 59020219 discloses an enteric composition for acid-labile active ingredients which comprises (under the enteric coating) an intermediate layer of a film-forming material, such as hydroxypropylmethylcellulose, hydroxypropylcellulose and hydroxypropylmethylcellulose phthalate with a content of higher fatty acids.

DE-A 3233764 proposes for enteric compositions an intermediate layer which is formed from a water-soluble cellulose ether and a water-soluble mono- or polybasic organic acid, such as citric acid, tartaric acid, and the like.

Combined use of irreversible proton pump inhibitors with antimicrobially-active ingredients does indeed show a good effect against Helicobacter in vitro. However, the clinical effect achieved with this combined use is disappointing. Of practical inconvenience is the great delay in the onset of action.

SUMMARY OF THE INVENTION

The action of an antimicrobially-active ingredient on Helicobacter surprisingly is enhanced by administering pantoprazole in slow-release dosage form (extended release form). It must be regarded as particularly surprising that, in addition, administration of the slow-release pantoprazole results in the onset of action taking place significantly faster than on administration in a form without retarding such release. The duration of treatment until Helicobacter is eradicated is shortened, saving considerable amounts of antibiotic and acid inhibitor.

The invention thus relates to oral pharmaceutical compositions in pellet or tablet form for combined use of pantoprazole with an antimicrobially-active ingredient for treatment of disorders caused by Helicobacter, wherein pantoprazole is present at least partly in slow-release form.

DETAILS

In connection with the present invention, pantoprazole is the compound, 5-difluoromethoxy-2-[(3,4-dimethoxy-2-pyridinyl)methylsulfinyl]-1H-benzimidazole, its salts and solvates (e.g. hydrates), in particular the sodium salt with one and a half molecules of water of crystallization (pantoprazole Na×1.5 $H_2O$).

Examples of suitable antimicrobially-active ingredients (active against Helicobacter and, in particular, against *Helicobacter pylori*) are enumerated in European Patent Application EP-A 0282131. These active ingredients include, for example, bismuth salts (such as bismuth subcitrate or bismuth subsalicylate), sulfonamides, nitrofurans (such as nitrofurazone, nitrofurantoin or furazolidone), metronidazole, tinidazole, nimorazole or antibiotics. Examples of antibiotics which may be mentioned in this connection are, arranged according to particular classes of active ingredient: aminoglycosides, such as gentamicin, neomycin, kanamycin, amikacin or streptomycin; macrolides, such as erythromycin, azithromycin, clarithromycin, clindamycin or rifampicin; penicillins, such as penicillin G, penicillin V, ampicillin, mezlocillin or amoxicillin; polypeptides, such as bacitracin or polymyxin; tetracylines, such as tetracyline, chlorotetracycline, oxytetracycline, minocycline or doxycycline; carbapenems, such as imipenem, loracarbef, meropenem or panipenem; cephalosporins, such as cefalexin, cefoxitin, cefuroxime axetil, cefotaxime, cefpodoxim proxetil, cefaclor, cefadroxil or cephalothin; gyrase inhibitors, such as ciprofloxacin, norfloxacin, ofloxacin or pefloxacin, or other different antibiotics, such as chloramphenicol.

Particularly worthy of mention in this connection is also the conjoint administration of pantoprazole with a plurality of antimicrobially-active ingredients, for example with a combination of bismuth salt and/or tetracycline with metronidazole, or with the combination of amoxicillin or clarithromycin with metronidazole.

Antimicrobially-active ingredients which may be emphasized are erythromycin, azithromycin, clarithromycin, clindamycin, rifampicin, ampicillin, mezlocillin, amoxicillin, tetracycline, minocycline, doxycycline, imipenem, meropenem, cefalexin, cefuroxime axetil, cefpodoxime proxetil, cefaclor, cefadroxil, ciprofloxacin, norfloxacin, ofloxacin and pefloxacin.

Clarithromycin and amoxicillin may be mentioned as antimicrobially-active ingredients which should be particularly emphasized.

Combined administration means, for the purpose of the present invention, fixed and, in particular, free combinations, i.e. either slow-release pantoprazole and the antimicrobially-active ingredient are present together in one dosage unit, or slow-release pantoprazole and antimicrobially-active ingredient, which are present in separate dosage units, are administered in direct succession or at a relatively large time interval; a relatively large time interval means a time span up to a maximum of 24 hours. For use as separate dosage units, these are preferably made available together in one pack. For example, the two dosage units are packed together in blister-packs which are designed with regard to the relative arrangement of the two dosage units with respect to one another, the inscription and/or coloring in a manner known per se so that the times for taking the individual components (dosage regimen) of the two dosage units are evident to a patient.

A dosage unit means, in particular, a medicinal dosage form in which slowing of pantoprazole release is achieved with as few problems as possible. This includes, in particular, tablets, coated tablets or pellets, and microtablets in capsules, with the dosage form advantageously being designed so that the two active-ingredient components (pantoprazole on the one hand and antimicrobially-active ingredient on the other hand) are released, or made available effectively for the body, in such as way that an optimal active ingredient profile, and thus action profile, is achieved.

It is possible to use (for retarding release) various types and degrees of retardation so that a pantoprazole plasma level, which persists as long as possible and is sufficient for raising pH, is ensured.

The pharmaceutical formulation of the antimicrobially-active ingredient is carried out as is familiar per se to the skilled worker for the individual active ingredient.

Rapid release of part of the pantoprazole and extending release of another part can be achieved, for example, also by layered tablets or multilayer tablets, in which case part of the pantoprazole is present in an outer coating in a form without retarding its release; this is followed by another coating containing the antimicrobially-active ingredient and then the core with the pantoprazole, whose release is extended in a suitable manner.

The details of how to achieve slowing of or extending release are familiar to the skilled worker on the basis of his expert knowledge. The skilled worker is likewise familiar with suitable ancillary substances and vehicles for the required dosage forms (pharmaceutical formulations). Besides solvents, tablet auxiliary substances and other active ingredient excipients it is possible to use, for example, tablet-coating compositions, plasticizers, antioxidants, preservatives, dyes, etc. Where incompatibilities between the active ingredients or between the active ingredients and ancillary substances are expected, suitable separating layers are provided where appropriate (for example in layered or multi-layer tablets).

The dosage of the active ingredients depends greatly on the nature of the antimicrobially-active ingredients used. A typical dosage for pantoprazole can be regarded as being a daily dose of from about 0.01 to about 20, preferably from 0.05 to 5, in particular from 0.1 to 1.5, mg/kg of body weight, where appropriate in the form of a plurality of single doses. Penicillins, such as amoxicillin, are administered in a daily dose of from about 5 to 40, preferably from 10 to 20, mg/kg of body weight.

Because of a great tendency to decompose in a neutral and, in particular, acidic environment, which also results in highly colored decomposition products, for oral compositions, it is necessary on the one hand to keep pantoprazole in an alkaline environment and, on the other hand, to protect it from exposure to acids. It is generally known to coat tablets or pellets which contain an acid-labile active ingredient with an enteric coating which, after passage through the stomach, rapidly dissolves in the alkaline medium in the intestine. In the case of pantoprazole, which in very acid-labile, it is necessary to process it in the tablet core or in pellets in the form of its alkaline salts, for example as sodium salts, or together with alkaline substances. Since the substances suitable for enteric coatings contain free carboxyl groups, a problem arises when the enteric coating is partly or even completely dissolved from the inside because of the alkaline medium in the interior, and the free carboxyl groups promote decomposition of the active ingredients. It is therefore necessary to provide a sealing intermediate layer (subcoating) between the enteric coating and the alkaline tablet core. EP-A 0244380 proposes to coat cores which contain the active ingredient together with alkaline compounds or as alkaline salt with at least one layer, which is soluble in water or rapidly disintegrates in water, of nonacidic, inert pharmaceutically-acceptable substance before the enteric layer is applied.

The intermediate layer or intermediate layers act as pH-buffering zones in which hydrogen ions, which diffuse in from the outside, are able to react with the hydroxyl ions which diffuse out of the alkaline core. In order to increase the buffer capacity of the intermediate layer, it is proposed to incorporate buffer substance into the intermediate layer (s). It is possible in practice by this method to obtain rather stable compositions. However, relatively thick intermediate layers are required to prevent the unsightly discoloration which occurs even on only slight decomposition. In addition, considerable effort must be made to avoid traces of moisture during manufacture.

It is a further aim within the scope of the present invention to provide an oral pharmaceutical composition with delayed and controlled release of active ingredients in pellet or tablet form for pantoprazole, which is distinguished by great resistance to decomposition and discoloration of the active ingredient caused by moisture and other effects.

This aim is particularly advantageously achieved by providing at least one release-slowing intermediate layer of water-insoluble film former, which at the same time represents a barrier for mutual interactions between the active ingredient with an alkaline reaction and the enteric coating with an acidic reaction.

In this connection, film formers are regarded as insoluble in water when they cannot be dissolved in water without further additions (organic solvents, detergents, alkalizing substances, etc.).

The invention therefore also relates to an oral pharmaceutical composition in pellet or tablet form for acid-labile irreversible proton pump inhibitors comprising an alkaline pellet or tablet core, at least one release-slowing, release-controlling intermediate layer and an outer enteric layer which is soluble in the small intestine, wherein the intermediate layer for the pharmaceutical composition is formed from a water-insoluble film former, the film former being applied from anhydrous solution or aqueous dispersion.

The slowing of release can be achieved, for example, by a semipermeable membrane, as disclosed in numerous patents (e.g. EP B 0185331).

The details of how to achieve slowing of release are familiar to the skilled worker on the basis of his expert knowledge. The skilled worker is likewise familiar with suitable ancillary substances and vehicles for the required dosage forms (pharmaceutical formulations). Besides solvents, tablet ancillary substances and other active ingredient excipients it is possible to use, for example, tablet-coating compositions, plasticizers, antioxidants, preservatives, dyes, etc. Where incompatibilities between the active ingredients or between the active ingredients and ancillary substances are expected, suitable separating layers are provided where appropriate.

The oral pharmaceutical compositions according to the invention are distinguished from the prior art by controlled release of active ingredients and increased stability. It is particularly advantageous to keep the intermediate layer (which controls the release of active ingredients) very thin (between 20 and 80, preferably between 40 and 60, μm), which leads to a considerable saving of material and shorter processing times. The insolubility of the intermediate layer in water means that the application of the enteric layer in the form of aqueous suspensions is not critical because there can be no dissolution of the intermediate layer. Furthermore, oral pharmaceutical compositions with a considerably smoother surface are obtained, which not only leads to a better visual appearance but also technically simplifies an imprinting process for tablets.

For a basic reaction of the pellet or tablet core it is mixed (where required increase in pH is not achieved simply by using an active-ingredient salt) with an inorganic base. Mention may be made in this connection of, for example, the pharmacologically-suitable alkali-metal, alkaline-earth-metal or earth-metal salts of weak acids and the pharmacologically-suitable hydroxides and oxides of alkaline-earth and earth metals. Sodium carbonate may be mentioned as a base to be emphasized by way of example.

Besides filler and binder, other ancillary substances, in particular lubricants and nonstick agents, and tablet disintegrants, are used in the manufacture of the tablet cores. A suitable binder is, in particular, polyvinylpyrrolidone in various degrees of polymerization. Examples of lubricants and nonstick agents which may be mentioned are higher fatty acids and their alkali-metal and alkaline-earth-metal salts, such as calcium stearate. Suitable tablet disintegrants are, in particular, chemically inert agents. Tablet disintegrants which may be mentioned as preferred are crosslinked polyvinylpyrrolidone, crosslinked sodium carboxymethylcelluloses and sodium starch glycolate.

Examples of film-forming polymers which can be used in the water-insoluble release-slowing intermediate layer(s) (to be applied to the pellet or tablet core) include ethylcellulose, polyvinyl acetate, Eudragit® RS, Eudragit® RL, etc. (Each of Eudragit® RS and Eudragit® RL is an ammonio methacrylate copolymer.) The release rate can be controlled not only by incorporating therein suitable water-soluble pore formers, such as PEG, lactose, mannitol, sorbitol, HPMC, etc., but also by the thickness of the coating layer applied.

The solvents or dispersants used for the release-controlling polymer dispersion are non-aqueous organic solvents, such as alcohols, ketones or halogenated hydrocarbons or mixtures of such solvents.

It is possible in a similar way to use osmotic systems with semipermeable membranes of cellulose acetate, cellulose acetate butyrate, cellulose acetate propionate, as described in U.S. Pat. Nos. 3,845,770, 3,916,899, 4,036,227, 4,093,708, 4,096,238, 4,135,514 and 4,142,526, to control the release of active ingredients. These can be coated with aqueous dispersions of enteric lacquers without changing release rate.

Examples of suitable polymers for the enteric coating are methacrylic acid/methyl methacrylate copolymer or methacrylic acid/ethyl methacrylate copolymer (Eudragit® L) or cellulose derivatives, such as carboxymethylethylcellulose (CMEC, Duodcel), cellulose acetate phthalate (CAP), cellulose acetate trimellitate (CAT), hydroxypropylmethylcellulose phthalate (HP50, HPSS), hydroxypropylmethylcellulose acetate succinate (HPMCAS) or polyvinyl acetate phthalate, to which it is also possible to add, if desired, plasticizer (such as propylene glycol) and/or other additives and ancillary substances (e.g. buffers, bases, such as, preferably, aluminum hydroxide, or pigments).

The layers are applied in conventional ways using equipment customary for these purposes.

EXAMPLES

The following formulation examples explain the invention in detail without restricting it.

Example 1

Tablets:

| I. | Production of uncoated core: | | |
|---|---|---|---|
| | a) | Pantoprazole Na × 1.5 H2O | 45.1 mg |
| | b) | Sodium carbonate | 10.0 mg |
| | c) | Mannitol | 20.0 mg |
| | d) | EPMC 2910 3 cps | 25.0 mg |
| | e) | HPMC 2910 15 cps | 4.0 mg |
| | f) | Calcium stearate | 2.1 mg |
| | | | 106.2 mg | a) is mixed with one part of b), c) and d). The remainder of b) and c) is added to the clear aqueous solution of e), and the pH is adjusted to >10 with b). This solution is used for fluidized bed granulation. The remainder of d) and f) is added to the dried granules, and the granules are compressed in a suitable tabletting machine.

| II. | Release-slowing layer | | |
|---|---|---|---|
| | g) | Ethylcellulose | 9.85 mg |
| | h) | Lactose micronized | 2.37 mg |
| | i) | Propylene glycol | 0.98 mg |
| | j) | Ammonia 25% | 0.80 mg |
| | | | 14.00 mg | g) is dissolved in 165 ml of isopropanol to prepare solution (A). A fine suspension of h) in 165 ml of isopropanol is prepared using a rotor-stator agitator, and subsequently i) and j) are stirred in using a suitable agitator to prepare suspension (B). The solution (A) and the suspension (B) are combined.

The tablet cores obtained from I are coated to an adequate layer thickness with the suspension obtained above in suitable apparatus.

| III. | Enteric coating: | | |
|---|---|---|---|
| | 1) | Eudragit ® L | 13.64 mg |
| | m) | Triethyl citrate | 1.36 mg |
| | | | 15.00 mg | l) is diluted with 140 ml of water, and m) is added. The resulting dispersion is screened before processing. The dispersion from III is sprayed onto the presealed cores obtained from II in suitable equipment.

Example 2

Tablets:

I. Production of the uncoated core:
Production of the cores took place as in Example I point I.
II. Release-slowing layer:

| | | |
|---|---|---|
| g) | Polyvinyl acetate | 9.15 mg |
| h) | Lactose micronized | 2.27 mg |
| i) | Propylene glycol | 0.91 mg |
| j) | Ammonia 25% | 0.80 mg |
| | | 13.13 mg | g) is dissolved in 150 ml of a 1:1 acetone/chloroform mixture to prepare a solution (A).

A fine dispersion of h) in 150 ml of a 1:1 acetone/choroform mixture is prepared using a rotor-stator agitator, and subsequently i) and j) are stirred in using a suitable agitator to prepare a suspension (B). Solution (A) and suspension (B) are combined.

The tablet cores obtained in I are coated to a sufficient layer thickness with the suspension obtained above in suitable apparatus.

III. Enteric coating:

| | | |
|---|---|---|
| 1) | Eudragit ® L | 13.64 mg |
| m) | Triethyl citrate | 1.36 mg |
| | | 15.00 mg | l) is diluted with 135 ml of water, and m) is added. The dispersion is screened before processing.

The dispersion from III is sprayed onto the presealed cores obtained in II in suitable equipment.

Example 3

Pellets:

I. Starter Pellets

| | | |
|---|---|---|
| a) | Sucrose pellets (0.7–0.85 mm) | 950.0 g |
| b) | Hydroxypropylmethylcellulose 2910 (USP) | 40.0 g |
| c) | Propylene glycol | 9.9 g |
| d) | NaOH | 0.1 g | a) is sprayed with an aqueous solution of b), c) and d) in a fluidized bed (Wurster method).

II. Active pellets

| | | |
|---|---|---|
| e) | Pantoprazole Na × 1.5 H | 403.0 g |
| f) | Hydroxypropylmethylcellulose 2910 (USP) | 403.0 g |
| g) | Propylene glycol | 201.5 g |
| h) | NaOH | 1.0 g | f), g), h), e) are successively dissolved in 4 liters of purified water and sprayed onto 900 g of the pellets obtained in I in a fluidized bed (Wurster method).

III. Presealed Pellets

A release-slowing layer is applied in analogy to the procedure described for tablets in a pan or fluidized bed.

IV. Enteric-coated Pellets

The coating is applied in analogy to the procedure described for the tablets in a pan or fluidized bed.

The pellets are subsequently packed into capsules of suitable size (e.g. size 1).

Example 4

Pellets:

I. Active Pellets

| | | |
|---|---|---|
| c) | Pantoprazole Na × 1.5 H$_2$O | 403.0 g |
| d) | Na carbonate | 87.3 g |
| e) | Microcrystalline cellulose (Avicel PH101) | 117.0 g |
| f) | Na carboxymethylcellulose | 18.0 g | c)–f) are premixed dry and subsequently moistened to a paste-like consistency with a solution of Na carbonate and Na carboxymethylcellulose in water in a conventional kneader or high-speed mixer. The resulting composition is then extruded and shaped into pellets by the extruder/rounder method familiar to the skilled worker.

The moistened pellets are dried in suitable equipment (drying oven, fluidized bed, etc.).

III. Release-slowing Layer:

The release-slowing layer is applied in analogy to the procedure described for tablets in a pan or fluidized bed.

IV. Enteric-coated Pellets

The coating is applied in analogy to the procedure described for tablets in a pan or fluidized bed.

The pellets are subsequently packed into capsules of suitable size (e.g. size 1).

The invention and its advantages are readily understood from the foregoing description. As is apparent, various changes can be made in the products and methods without departing from the spirit and scope of the invention or sacrificing its material advantages. The products and processes hereinbefore described are merely illustrative of a preferred embodiments of the invention.

What is claimed is:

1. A delayed and controlled release oral pharmaceutical composition comprising pantoprazole, an alkaline pellet or tablet core, at least one intermediate layer controlling release of active ingredient and an outer enteric layer which is soluble in the small intestine.

2. An oral pharmaceutical composition as claimed in claim 1, wherein at least one intermediate layer is formed from a water-insoluble, release-slowing film former.

3. An oral pharmaceutical composition as claimed in claim 2, wherein the film former is one which has been applied from a solution or dispersion.

4. An oral pharmaceutical composition as claimed in claim 2, wherein the intermediate layer contains, as water-insoluble, release-slowing film former, water-insoluble cellulose ether and/or polyvinyl acetate.

5. An oral pharmaceutical composition as claimed in claim 2, wherein the outer enteric layer, which is soluble in the small intestine, comprises methacrylic acid/methyl methacrylate copolymer or methacrylic acid/ethyl methacrylate copolymer.

6. An oral pharmaceutical composition as claimed in claim 1, wherein the outer enteric layer comprises a cellulose-based coating.

7. An oral pharmaceutical composition as claimed in claim 6, wherein the cellulose-based coating is a member selected from the group consisting of carboxymethylethylcellulose, cellulose acetate phthalate, cellulose acetate trimellitate, hydroxypropylmethylcellulose phthalate and hydroxypropylmethylcellulose acetate succinate.

8. An oral pharmaceutical composition as claimed in claim 1, wherein the intermediate layer further comprises a member selected from the group consisting of a pore former, plasticizer, buffer, base and pigment.

9. A process for producing an oral pharmaceutical composition in pellet or tablet form for pantoprazole, as active ingredient, which comprises a) incorporating the active ingredient as an alkaline salt and/or with addition of an alkaline substance in a pellet or tablet core, b) applying thereto at least one release-slowing intermediate layer comprising a water-insoluble, release-slowing film former and c) subsequently applying an outer enteric layer which is soluble in the small intestine.

10. A process as claimed in claim 9, wherein the water-insoluble, release-slowing film former for the intermediate layer is applied in solution or dispersion form in a non-aqueous organic solvent or other solvent mixture.

11. An oral pharmaceutical composition as claimed in claim 1 wherein part of the pantoprazole is in a controlled (extended) release form and part of the pantoprazole is in a form without retarding its release (rapid release form).

12. An oral pharmaceutical composition as claimed in claim 2, wherein the intermediate layer contains, as water-insoluble, release-slowing film former, ethylcellulose.

13. An oral pharmaceutical composition as claimed in claim 2, wherein the intermediate layer contains, as water-insoluble, release-slowing film former, ammonio methacrylate copolymer.

14. An oral pharmaceutical composition as claimed in claim 2, wherein the intermediate layer contains, as water-insoluble, release-slowing film former, polyvinyl alcohol.

15. An oral pharmaceutical composition as claimed in claim 1, wherein the intermediate layer has a thickness of from 20 to 80 microns.

16. An oral pharmaceutical composition as claimed in claim 1, wherein the intermediate layer has a thickness between 40 and 60 microns.

* * * * *